US012642767B2

(12) United States Patent
Wei et al.

(10) Patent No.: US 12,642,767 B2
(45) Date of Patent: Jun. 2, 2026

(54) IRINOTECAN LIPOSOME PREPARATION, AND PREPARATION AND APPLICATION THEREOF

(71) Applicant: HighField BioPharmaceutical Corporation, HangZhou (CN)

(72) Inventors: Xiaohui Wei, Shanghai (CN); Bingqi Jiang, Shanghai (CN)

(73) Assignee: HighField BioPharmaceutical Corporation, HangZhou (CN)

( * ) Notice: Subject to any disclaimer, the term of this patent is extended or adjusted under 35 U.S.C. 154(b) by 1124 days.

(21) Appl. No.: 17/290,263

(22) PCT Filed: Oct. 11, 2019

(86) PCT No.: PCT/CN2019/110542
§ 371 (c)(1),
(2) Date: Apr. 30, 2021

(87) PCT Pub. No.: WO2020/093836
PCT Pub. Date: May 14, 2020

(65) Prior Publication Data
US 2022/0031618 A1 Feb. 3, 2022

(30) Foreign Application Priority Data

Nov. 5, 2018 (CN) .......................... 201811305299.6

(51) Int. Cl.
| | |
|---|---|
| A61K 9/127 | (2025.01) |
| A61K 9/1271 | (2025.01) |
| A61K 9/1277 | (2025.01) |
| A61K 31/4745 | (2006.01) |
| A61K 47/20 | (2006.01) |

(52) U.S. Cl.
CPC .......... *A61K 9/1271* (2013.01); *A61K 9/1277* (2013.01); *A61K 31/4745* (2013.01); *A61K 47/20* (2013.01)

(58) Field of Classification Search
CPC ............... A61K 9/1271; A61K 9/1277; A61K 31/4745; A61K 47/20
See application file for complete search history.

(56) References Cited

U.S. PATENT DOCUMENTS

| | | | | |
|---|---|---|---|---|
| 2017/0224715 A1* | 8/2017 | Hayes | ................ | A61K 31/4196 |
| 2017/0266295 A1* | 9/2017 | Kan | .................... | A61K 31/704 |

FOREIGN PATENT DOCUMENTS

| | | | | |
|---|---|---|---|---|
| CN | 107260680 A | * | 10/2017 | ........... A61K 31/506 |
| EP | 2494960 A1 | * | 9/2012 | ........... A61K 31/136 |

OTHER PUBLICATIONS

Zhigaltsev et al.; Formation of drug-arylsulfonate complexes inside liposomes: A novel approach to improve drug retention; 2006, Science Direct, 110, 378-386 (Year: 2006).*
CN-107260680-A machine translation (Year: 2017).*
Dasatinib; https://pubchem.ncbi.nlm.nih.gov/compound/3062316 (site accessed Feb. 2024) (Year: 2016).*
Irinotecan; https://pubchem.ncbi.nlm.nih.gov/compound/Irinotecan (site accessed Feb. 2024) (Year: 2016).*
Drummond et al.; Improved Pharmacokinetics and Efficacy of a Highly Stable Nanoliposomal Vinorelbine; The American Society for Pharmacology and Experimental Therapeutics; The Journal of Pharmacology and Experimental Therapeutics vol. 328, No. 1 321-330, 2009 (Year: 2009).*

* cited by examiner

*Primary Examiner* — Robert A Wax
*Assistant Examiner* — John W Lippert, III
(74) *Attorney, Agent, or Firm* — IPRTOP LLC

(57) ABSTRACT

An irinotecan liposome preparation, a preparation method, and use thereof. The irinotecan liposome includes: irinotecan, a liposome carrier, an internal aqueous phase located inside a liposome membrane and an external aqueous phase located outside the liposome membrane, the irinotecan being encapsulated in the internal aqueous phase; a sulfonate gradient exists between the internal aqueous phases inside the liposome membrane and the external aqueous phase outside the liposome membrane. The liposome takes monovalent sulfonate and disulfonate as the internal aqueous phases, encapsulates the irinotecan in the internal aqueous phases of the liposome in the form of insoluble sulfonate or disulfonate, and has a good sustained-release effect.

4 Claims, 3 Drawing Sheets

IRINOTECAN LIPOSOME PREPARATION, AND PREPARATION AND APPLICATION THEREOF

TECHNICAL FIELD

The present disclosure belongs to the technical field of nano-drug delivery, in particular to an irinotecan liposome preparation, and preparation and application thereof.

BACKGROUND

Irinotecan (CPT-11), a semi-synthetic derivative of camptothecin, is an effective drug for treating metastatic colon cancer. Camptothecins can specifically bind to topoisomerase I which induces reversible single-strand breaks, thereby resulting in unwinding of DNA duplex structure. Irinotecan and its active metabolite SN-38 can bind to a topoisomerase I-DNA complex, so as to prevent the re-ligation of broken single strands. Current studies show that the cytotoxicity of irinotecan is due to the interaction between replicase and the triple complex of topoisomerase I-DNA-irinotecan (or SN-38) during the synthesis of DNA, so that the DNA double strands break.

Currently, commercially available irinotecan products include irinotecan hydrochloride injections, freeze-dried powder injections, and liposome injections. Of those, irinotecan hydrochloride is a hydrochloride salt of irinotecan, which has good water solubility. Once the irinotecan hydrochloride injection is intravenously administered, in a slightly alkaline physiological environment, the lactone ring of free irinotecan is likely to undergo ring opening to form a carboxylate form, thereby losing its activity and reducing the efficacy of the drug. Meanwhile, the freeze-dried powder injection of irinotecan hydrochloride has relatively serious toxic and side effects, which are mainly manifested as neutropenia and delayed diarrhea.

In October, 2015, the FDA approved an irinotecan liposome drug, Onivyde, for use in treatment of advanced pancreatic cancer. Onivyde employed the triethylamine salt of sucrose octasulfate (FIG. 1a) as an internal aqueous phase, and encapsulated irinotecan in the internal aqueous phase of liposome by using the triethylamine gradient between the internal and external aqueous phases of liposome, to form an irinotecan-sucrose octasulfate salt, achieving the effect of sustained release in vivo (Drummond, D. C. et al., Development of a highly active nanoliposomal irinotecan using a novel intraliposomal stabilization strategy[J]. Cancer Research, 2006, 66 (6), 3271-3277.) As a key excipient of Onivyde liposome, triethylamine sucrose octasulfate is not only expensive, but also complex to prepare. Firstly, a sodium salt of sucrose octasulfate is converted into sucrose octasulfate by ion exchange resin, which is then titrated with triethylamine to give the triethylamine sucrose octasulfate. Moreover, it is also reported that the sucrose octasulfate may have an activity similar to growth factors (QIU, Yongfeng et al., Review on the Application of Sucrose Octasulfate, *Medical and Health (Citation Edition)*, Vol. 5, 2017, P. 286.)

In the published Chinese patents involving irinotecan hydrochloride or irinotecan liposome, the used gradients of drug loading focus on the ammonium sulfate gradient (e.g., CN103120645B, entitled "Liposome of Irinotecan or Irinotecan hydrochloride and Preparation Method Thereof") and proton concentration gradient method (e.g., CN1960729B, entitled "Irinotecan Preparation"). Liposomes of irinotecan or irinotecan hydrochloride prepared by means of ammonium sulfate gradient and proton concentration gradient cannot effectively achieve an effect of sustained release, e.g., the liposome of irinotecan prepared by the ammonium sulfate gradient (CN105796495A) exhibits a half-life of drug of 8.90 hrs in rats.

Therefore, there is a need of developing active drug loading gradients based on other types of ammonium salts or triethylamine salts for the preparation of irinotecan liposomes, which are more easily available and can achieve good sustained-release effect in vivo.

SUMMARY OF THE DISCLOSURE

The present disclosure provides an irinotecan liposome preparation, and preparation and use thereof.

A first aspect of the present disclosure provides an irinotecan liposome preparation including an irinotecan liposome, the irinotecan liposome including: irinotecan, a liposome carrier, an internal aqueous phase located inside a liposome membrane, and an external aqueous phase located outside the liposome membrane, the irinotecan being encapsulated in the internal aqueous phase; a sulfonate gradient exists between the internal aqueous phase inside the liposome membrane and the external aqueous phase outside the liposome membrane.

In an embodiment of the present disclosure, the liposome is a single-chamber liposome.

In an embodiment of the present disclosure, the liposome has a particle size in a range of 30 nm to 200 nm.

In an embodiment of the present disclosure, the liposome has a particle size in a range of 50 nm to 120 nm.

In an embodiment of the present disclosure, the liposome has a particle size in a range of 90 nm to 110 nm.

In an embodiment of the present disclosure, the liposome has a D95 of less than or equal to 200 nm. D95 refers to the corresponding particle size value when the cumulative distribution percentage of the liposomes from small to large reaches 95%, that is, in the liposomes, the number of liposome particles with a particle size less than D95 accounts for 95% of the total number of the liposome particles.

In an embodiment of the present disclosure, the liposome has a D95 of less than or equal to 120 nm. D95 refers to the corresponding particle size value when the cumulative distribution percentage of the liposomes from small to large reaches 95%, that is, in the liposomes, the number of liposome particles with a particle size less than D95 accounts for 95% of the total number of the liposome particles.

In an embodiment of the present disclosure, the liposome has a D95 of less than or equal to 110 nm. D95 refers to the corresponding particle size value when the cumulative distribution percentage of the liposomes from small to large reaches 95%, that is, in the liposomes, the number of liposome particles with a particle size less than D95 accounts for 95% of the total number of the liposome particles.

In an embodiment of the present disclosure, the internal aqueous phase includes an aqueous sulfonate solution; and the external aqueous phase is a physiological isotonic solution.

In an embodiment of the present disclosure, the cation of irinotecan and the sulfonate anion within the internal aqueous phase form an insoluble salt.

In an embodiment of the present disclosure, the sulfonate is monovalent sulfonate and/or disulfonate.

In an embodiment of the present disclosure, the monovalent sulfonate may be one or more selected from the group consisting of ammonium methanesulfonate, ammonium 4-hydroxybenzenesulfonate, triethylamine methanesulfonate, and triethylamine 4-hydroxybenzenesulfonate.

In an embodiment of the present disclosure, the disulfonate may be one or more selected from the group consisting of ammonium ethanedisulfonate, ammonium propanedisulfonate, triethylamine ethanedisulfonate, and triethylamine propanedisulfonate.

In an embodiment of the present disclosure, the internal aqueous phase of the liposome has a monovalent sulfonate ion concentration of 100 mM to 800 mM.

In an embodiment of the present disclosure, the internal aqueous phase of the liposome has a monovalent sulfonate ion concentration of 200 mM to 700 mM.

In an embodiment of the present disclosure, the internal aqueous phase of the liposome has a disulfonate ion concentration of 50 mM to 500 mM.

In an embodiment of the present disclosure, the internal aqueous phase of the liposome has a disulfonate ion concentration of 100 mM to 400 mM.

In an embodiment of the present disclosure, the physiological isotonic solution is selected from 5% (w/v) aqueous glucose solution, 10% (w/v) aqueous sucrose solution or 0.9% (w/v) aqueous sodium chloride solution.

In an embodiment of the present disclosure, the internal aqueous phase of the liposome has a pH value of 4.0-9.0.

In an embodiment of the present disclosure, the internal aqueous phase of the liposome has a pH value of 4.5-8.0.

In an embodiment of the present disclosure, in the irinotecan liposome preparation, the irinotecan has a concentration of greater than or equal to 0.86 mg/ml.

In an embodiment of the present disclosure, the drug-liposome molar ratio of the irinotecan to the liposome is greater than or equal to 0.1.

In an embodiment of the present disclosure, the components of the liposome include phospholipids, cholesterols and PEGylated phospholipids.

In an embodiment of the present disclosure, the polyethylene glycol in the PEGylated phospholipids has a molecular weight of 50-10000.

In an embodiment of the present disclosure, the polyethylene glycol in the PEGylated phospholipid has a molecular weight of 2000.

In an embodiment of the present disclosure, the molar ratio of the phospholipids, the cholesterols and the PEGylated phospholipids is (30-80):(0.1-40):(0.1-30).

In an embodiment of the present disclosure, the molar ratio of the phospholipids, the cholesterols and the PEGylated phospholipids is 55:40:5.

In an embodiment of the present disclosure, the external aqueous phase of the liposome is a sucrose solution with a mass concentration of 10%.

A second aspect of the present disclosure provides a method for preparing the irinotecan liposome preparation which is an active loading method, including the following steps:

(1) preparing a blank liposome, of which both the internal aqueous phase and the external aqueous phase include an aqueous sulfonate solution;

(2) preparing a blank liposome, of which the internal aqueous phase includes an aqueous sulfonate solution and the external aqueous phase includes a physiological isotonic solution to form a sulfonate concentration gradient between the internal and the external aqueous phases of the blank liposome; and (3) mixing the blank liposome obtained in Step (2) with an aqueous solution of an irinotecan soluble salt, incubating the mixture, and removing the free soluble irinotecan salt to obtain the irinotecan liposome.

In an embodiment of the present disclosure, the sulfonate is selected from monovalent sulfonate and/or disulfonate.

In an embodiment of the present disclosure, the monovalent sulfonate may be one or more selected from the group consisting of ammonium methanesulfonate, ammonium 4-hydroxybenzenesulfonate, triethylamine methanesulfonate, and triethylamine 4-hydroxybenzenesulfonate.

In an embodiment of the present disclosure, the disulfonate may be one or more selected from the group consisting of ammonium ethanedisulfonate, ammonium propanedisulfonate, triethylamine ethanedisulfonate, and triethylamine propanedisulfonate.

In an embodiment of the present disclosure, in Step (1) and Step (2), the aqueous sulfonate solution has a sulfonate concentration of 50 mM to 800 mM.

In Step (1) and Step (2), the aqueous sulfonate solution has a cation concentration of 50 mM to 800 mM.

In an embodiment of the present disclosure, in Step (1) and Step (2), the aqueous sulfonate solution has a pH value of 4.0-9.0.

In an embodiment of the present disclosure, in Step (1) and Step (2), the aqueous sulfonate solution has a pH value of 4.5-8.0.

In an embodiment of the present disclosure, in Step (1) and Step (2), when monovalent sulfonate is used, the aqueous sulfonate solution has a sulfonate ion concentration of 100 mM to 800 mM.

Further, in Step (1) and Step (2), when monovalent sulfonate is used, the aqueous sulfonate solution has a sulfonate ion concentration of 200 mM to 700 mM.

In an embodiment of the present disclosure, in Step (1) and Step (2), when disulfonate is used, the aqueous sulfonate solution has a cation concentration of 50 mM to 500 mM.

Further, when disulfonate is used, in Step (1) and Step (2), the aqueous sulfonate solution has a cation concentration of 100 mM to 400 mM.

In an embodiment of the present disclosure, in Step (2), the physiological isotonic solution may be selected from 5% (w/v) aqueous glucose solution, 10% (w/v) aqueous sucrose solution or 0.9% (w/v) aqueous sodium chloride solution.

In an embodiment of the present disclosure, in Step (2), the internal aqueous phase of the liposome has a pH value of 4.0-9.0.

Further, in Step (2), the internal aqueous phase of the liposome has a pH value of 4.5-8.0.

In an embodiment of the present disclosure, in Step (3), the drug-liposome molar ratio is greater than or equal to 0.1.

In an embodiment of the present disclosure, in Step (3), the soluble irinotecan salt is irinotecan hydrochloride.

The present disclosure provides the use of the irinotecan liposome as described above in preparation of a drug for treating colorectal cancer, lung cancer, breast cancer, or pancreatic cancer.

In an embodiment of the present disclosure, in the use, the irinotecan liposome preparation can allow more irinotecan to be present in the blood circulation in a form of active lactone ring, arrive at the tumor site, and convert into SN-38, thereby further improving the anti-tumor effect.

The present disclosure has the following benefits:

The irinotecan liposome preparation provided by the present disclosure improves the availability of raw materials and reduces the cost of the preparation, while simultaneously achieving stable loading of irinotecan, and has the advantages of high encapsulation efficiency and good storage stability. At the same time, the preparation has obvious sustained release property, which contributes to ensuring the in vivo stability and effectiveness of irinotecan hydrochloride and improving the efficacy of the drug. The irinotecan liposome of the present disclosure has long half-life in vivo and high bioavailability.

Figures 1A, 1B, 2:
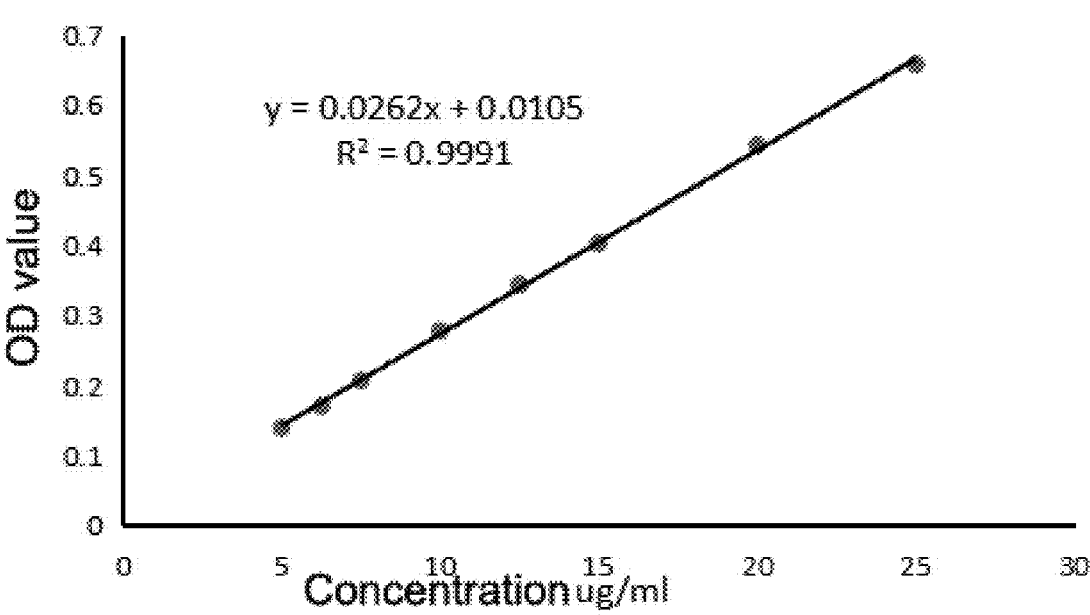
FIG. 1A: a chemical structure of monovalent sulfonic acid (left: methanesulfonic acid; right: 4-hydroxybenzenesulfonic acid)
FIG. 1B: a chemical structure of disulfonic acid (left: ethionic acid; right: propanedisulfonic acid)
FIG. 2: a UV standard curve of an aqueous solution of irinotecan hydrochloride.

DETAILED DESCRIPTION OF THE
EMBODIMENTS

By a large number of exploration experiments, the inventor found that the sulfonate anions in the internal aqueous phase of liposome can form insoluble salt with irinotecan cations, and in turn stably encapsulate irinotecan within the internal aqueous phase of liposome. On the basis, the present disclosure is completed.

The irinotecan liposome preparation of the present disclosure includes an irinotecan liposome, and the irinotecan liposome includes irinotecan and a liposome carrier.

The liposome has a liposome membrane with a bilayer structure. The liposome membrane is similar to a biofilm.

The carrier of the liposome includes phospholipid and cholesterol. The material and amount of the carrier of the liposome are not particularly limited in the present disclosure, as long as a stable, leak-free liposome membrane with a bilayer structure can be formed. These are all within the scope of the knowledge of persons skilled in the art.

Examples of the present disclosure exemplify that hydrogenated soybean phospholipid (HSPC) and distearoyl phosphatidylethanolamine-polyethylene glycol (DSPE-PEG) may be selected as the phospholipid. However, it is not limited thereto.

The PEG in the DSPE-PEG may have a molecular weight in a range of 50-10000. For example, the PEG in the DSPE-PEG has a molecular weight of 2000.

The molar ratio of HSPC, CHOL (cholesterol), and DSPE-PEG may be in a range of (30-80):(0.1-40):(0.1-30). For example, the molar ratio of HSPC, CHOL, DSPE-PEG may be 55:40:5.

The irinotecan liposome preparation further includes an internal aqueous phase located inside the liposome membrane and an external aqueous phase located outside the liposome membrane. The irinotecan is encapsulated in the internal aqueous phase.

There is a sulfonate gradient between the internal aqueous phase inside the liposome membrane and the external aqueous phase outside the membrane.

The ammonium salt gradient refers to the presence of differences between ammonium concentration gradients and pH values.

The triethylamine salt gradient refers to the presence of differences between triethylamine concentration gradients and pH values.

The internal aqueous phase is an aqueous sulfonate solution, and the irinotecan cation and the sulfonate ion form an insoluble salt, so that the irinotecan is encapsulated in the internal aqueous phase. The external aqueous phase is a physiological isotonic solution.

The physiological isotonic solution is selected from 5% (w/v) aqueous glucose solution, 10% (w/v) aqueous sucrose solution or 0.9% (w/v) aqueous sodium chloride solution.

% (w/w) refers to a mass percent concentration, that is, a mass of solute contained in 100 g of solution.

% (w/v) refers to a mass-by-volume percent concentration, that is, a mass of solute contained in 100 ml of solution.

The irinotecan liposome preparation may be a preparation for injectable administration.

The preparation for injectable administration may be selected from subcutaneously, intravenously, intramuscularly, or intrapelvically injectable dosage forms.

The cation of sulfonate may be selected from the group consisting of ammonium ion and triethylammonium ion.

The sulfonate may be selected from monovalent sulfonate and/or disulfonate. Of those, the monovalent sulfonate may be one or more selected from the group consisting of ammonium methanesulfonate, ammonium 4-hydroxybenzenesulfonate, triethylamine methanesulfonate, and triethylamine 4-hydroxybenzenesulfonate. The disulfonate may be one or more selected from the group consisting of ammonium ethanedisulfonate, ammonium propanedisulfonate, triethylamine ethanedisulfonate, and triethylamine propanedisulfonate.

The internal aqueous phase may have a pH of 4.0-9.0, preferably, 4.5-8.0.

When a monovalent sulfonate is used, the internal aqueous phase may have a sulfonate ion concentration of 100-800 mM, preferably, 200-700 mM.

When a disulfonate is used, the internal aqueous phase may have a sulfonate ion concentration of 50 mM to 500 mM, preferably, 100-400 mM.

The internal aqueous phase may have an irinotecan concentration of 0.1 mg/ml or higher.

The method for preparing the irinotecan liposome preparation of the present disclosure includes the following steps:

(1) preparing a blank liposome, of which both the internal aqueous phase and the external aqueous phase include an aqueous sulfonate solution;

(2) preparing a blank liposome, of which the internal aqueous phase includes an aqueous sulfonate solution and the external aqueous phase includes a physiological isotonic solution to form a sulfonate concentration gradient between the internal and the external aqueous phases of the blank liposome; and (3) mixing the blank liposome obtained in Step (2) with an aqueous solution of an irinotecan soluble salt, incubating the mixture, and removing the free soluble irinotecan salt to obtain the irinotecan liposome.

The sulfonate is selected from monovalent sulfonate and/or disulfonate.

The monovalent sulfonate may be one or more selected from the group consisting of ammonium methanesulfonate, ammonium 4-hydroxybenzenesulfonate, triethylamine methanesulfonate, and triethylamine 4-hydroxybenzenesulfonate.

The disulfonate may be one or more selected from the group consisting of ammonium ethanedisulfonate, ammonium propanedisulfonate, triethylamine ethanedisulfonate, and triethylamine propanedisulfonate.

In Step (1) and Step (2), when monovalent sulfonate is used, the aqueous sulfonate solution has a sulfonate ion concentration of 100 mM to 800 mM.

Further, in Step (1) and Step (2), when monovalent sulfonate is used, the aqueous sulfonate solution has a sulfonate ion concentration of 200 mM to 700 mM.

When a disulfonate is used, in Step (1) and Step (2), the aqueous sulfonate solution has a cation concentration of 50 mM to 500 mM.

Further, when disulfonate is used, in Step (1) and Step (2), the aqueous sulfonate solution has a cation concentration of 100 mM to 400 mM.

In Step (1) and Step (2), the aqueous sulfonate solution has a pH value of 4.0-9.0. The aqueous sulfonate solution may further have a pH value of 4.5-8.0.

In Step (2), the physiological isotonic solution may be selected from 5% (w/v) aqueous glucose solution, 10% (w/v) aqueous sucrose solution or 0.9% (w/v) aqueous sodium chloride solution.

In an embodiment of the present disclosure, in Step (2), the external aqueous phase has a pH value of 4.0-9.0. The external aqueous phase may further have a pH value of 5.0-8.0.

In an embodiment of the present disclosure, in Step (3), the drug-liposome ratio (i.e., the molar ratio of irinotecan to liposome) may be 0.1 or higher. The drug-liposome ratio may further be 0.15 or higher. The drug-liposome ratio may further be 0.20 or higher. The drug-liposome ratio may further be 0.25 or higher. The drug-liposome ratio may further be 0.3 or higher. The drug-liposome ratio may further be 0.5 or higher. The drug-liposome ratio may be 0.1-0.15. The drug-liposome ratio may be 0.1-0.2. The drug-liposome ratio may be 0.1-0.25. The drug-liposome ratio may be 0.1-0.3. The drug-liposome ratio may be 0.15-0.3. The drug-liposome ratio may be 0.3-0.5. The drug-liposome ratio may be 0.2-0.5.

In an embodiment of the present disclosure, in Step (3), the soluble irinotecan salt is irinotecan hydrochloride.

In the aqueous solution of soluble irinotecan salt, the irinotecan may have a concentration of greater than or equal to 10 mg/ml. The irinotecan may have a concentration of greater than or equal to 12 mg/ml. The irinotecan may have a concentration of greater than or equal to 15 mg/ml. For example, the irinotecan may have a concentration of 10 mg/ml, 12 mg/ml, or 15 mg/ml. The irinotecan may have a concentration of 10 mg/ml-12 mg/ml. The irinotecan may have a concentration of 12 mg/ml-15 mg/ml. The irinotecan may have a concentration of 10 mg/ml-15 mg/ml.

The present disclosure utilizes the active drug loading principle: a sulfonate ion gradient exists between the internal and the external aqueous phases of the liposome. The irinotecan hydrochloride in the external aqueous phase is partially ionized, and the un-ionized irinotecan passively diffuses into the internal aqueous phase of the liposome and combines with the hydrogen ion generated by the ionization of ammonium ion or triethylamine ion in the internal aqueous phase to form an irinotecan ion, which in turn forms a crystalline or amorphous insoluble salt with sulfonate ion, thereby encapsulating the irinotecan in the internal aqueous phase of liposome. At the same time, ammonia generated by the ionization of ammonium ion or triethylamine generated by the ionization of triethylamine ion in the aqueous phase of liposome continuously escapes from the internal aqueous phase of the liposome, thereby maintaining the hydrogen ion concentration in the internal aqueous phase of the liposome, allowing the irinotecan molecules in the internal aqueous phase of the liposome to continuously combine with hydrogen ion to form irinotecan cations which form precipitates with the sulfonate ions, until almost all of the irinotecan in the external aqueous phase is encapsulated in the internal aqueous phase of the liposomes. The liposome has high drug loading and high stability, and has superior sustained release effects.

Use of Irinotecan Liposome Preparation

Irinotecan is a semisynthetic, water-soluble, camptothecin-based derivative, which can be used to treat tumors including colorectal cancer, lung cancer, breast cancer, and pancreatic cancer.

The irinotecan liposome preparation of the present disclosure enables more irinotecan to exist in a form of active lactone ring in the blood circulation, arrive at the tumor site, and convert into SN-38, thereby further improving the anti-tumor effect. The irinotecan liposome of the present disclosure has long half-life in vivo and high bioavailability.

Before the specific embodiments of the present disclosure are further described, it should be understood that the scope of protection of the present disclosure is not limited to the following specific embodiments. It should also be understood that the terms used in the embodiments of the present disclosure are intended to describe the specific embodiments, rather than limiting the protection scope of the present disclosure. In the description and claims of the present disclosure, unless otherwise clearly stated in the context, the singular forms "a", "an" and "the" include the plural forms.

When numerical ranges are provided in the examples, it should be understood that both the endpoints of each range and any value between the two endpoints are available unless otherwise indicated. Unless otherwise defined, all technical and scientific terms used in the present disclosure have the same meaning as those commonly understood by those skilled in the art. In addition to the specific methods, equipment and materials used in the embodiments, according to the understanding of persons skilled in the art and the disclosure of the present disclosure, any methods, equipment and materials of the prior art that are similar to or equivalent to the methods, equipment and materials as described in the examples of the present disclosure can be used to realize the present disclosure.

Unless otherwise specified, the experimental methods, detection methods and preparation methods disclosed in the present disclosure all adopt the conventional pharmaceutics, pharmaceutical analysis, pharmaceutical chemistry, analytical chemistry, molecular biology, biochemistry and related conventional technologies in the technical field. These techniques have been well described in the prior art literature.

Embodiment 1 Method of Detecting Irinotecan Hydrochloride

In this Embodiment, a standard curve of irinotecan hydrochloride was established as follows.

Ultraviolet (UV) analysis was used: the detection device is TECAN Infinite®200 PRO; the detection wavelength is 369 nm; the detection temperature is 24° C.; the well plate for detection is Coming® 96 well plates, UV-transparent; and the detection volume is 200 μl.

2.5001 mg irinotecan hydrochloride was accurately weighed and dissolved in a 25-ml volumetric flask to give an aqueous solution of irinotecan hydrochloride with a concentration of 0.1000 mg/ml, which was mixed with ultrapure water and diluted in gradient to give a series of standard solutions of irinotecan hydrochloride with concentrations of 5 μg/ml, 6.25 m/ml, 7.5 μg/ml, 10 μg/ml, 12.5 m/ml, 15 μg/ml, 20 μg/ml and 25 μg/ml. The standard solutions of irinotecan hydrochloride with the above-described concentrations were detected with the UV method. The detection results are shown in Table 1.

TABLE 1

| UV Detection of Aqueous Solutions of Irinotecan Hydrochloride with Different Concentrations | | | | | |
|---|---|---|---|---|---|
| Concentration | UV Absorbance | | | | SD |
| (μg/ml) | 1 | 2 | 3 | Average | (±) |
| 5 | 0.1393 | 0.1382 | 0.1386 | 0.1387 | 0.001 |
| 6.25 | 0.1758 | 0.1689 | 0.1647 | 0.1698 | 0.006 |
| 7.5 | 0.2063 | 0.2050 | 0.2073 | 0.2062 | 0.001 |
| 10 | 0.2785 | 0.2761 | 0.2776 | 0.2774 | 0.001 |
| 12.5 | 0.3462 | 0.3412 | 0.3440 | 0.3438 | 0.002 |
| 15 | 0.4090 | 0.3967 | 0.4015 | 0.4024 | 0.006 |
| 20 | 0.5447 | 0.5401 | 0.5427 | 0.5425 | 0.002 |
| 25 | 0.6585 | 0.6570 | 0.6592 | 0.6582 | 0.001 |
| Y = 0.0262X + 0.0105 | | | $R^2$ = 0.9991 | | |

According to the results as shown in Table 1, the standard curve was established and the recovery rate was investigated. The working curve is shown in FIG. 2. The aqueous solution of irinotecan hydrochloride has a UV standard curve of: $Y=0.0262X+0.0105$ (n=8), $R^2=0.9991$; the recovery rate is in a range of 95%-105%; and the standard curve fits well.

Embodiment 2 Preparation and Characterization of Irinotecan Liposome Using Ammonium Methanesulfonate as the Internal Aqueous Phase The phospholipids used in this Embodiment are all purchased from Lipoid, Germany, in particular, hydrogenated soybean phospholipid (HSPC, molecular weight: 783.8); the PEGylated phospholipid is in particular distearyl phosphatidylethanolamine-PEG 2000 (DSPE-PEG2000); cholesterol (CHOL, molecular weight: 386.7); the irinotecan hydrochloride used was purchased from Aladdin Inc.; the methylsulfonic acid used was purchased from Sigma-Aldrich; and the ammonium hydroxide used was purchased from Aladdin Inc.

It should be indicated that all the phospholipids used in the following Embodiments were hydrogenated soybean phospholipid from Lipoid Company; all the PEGylated phospholipids used were distearyl phosphatidylethanolamine-PEGs from Lipoid Company; all the cholesterol used were cholesterols from Lipoid; and all the irinotecan hydrochloride used were purchased from Aladdin Company.

2.1 Preparation of Irinotecan Liposome

The specific preparation was as follows:

Step (1): 479.9 mg of hydrogenated soybean phospholipid, 160.9 mg of cholesterol and 160.8 mg of distearyl phosphatidylethanolamine-PEG 2000 were accurately weighed, and thoroughly dissolved and mixed by adding an appropriate amount of ethanol to give a mixed solution of lipids in ethanol.

Step (2): 2.131 ml of methanesulfonic acid solution was accurately taken, titrated with ammonium hydroxide to a pH of 4.0-6.0, and diluted with ddH₂O to 50 ml to give a 650 mM buffer of ammonium methanesulfonate at a pH of 4.0-6.0.

Step (3): the mixed solution of lipids in ethanol obtained in Step (1) was added with 10 ml of 650 mM ammonium methanesulfonate buffer with a pH of 4.0-6.0, and placed in a stirring water bath at 70° C. for 30 minutes, so that the liposome was thoroughly hydrated to give a homogeneous liposome suspension.

Step (4): the liposome suspension obtained in Step (3) was sequentially extruded through polycarbonate films with different pore sizes for 10 times each using a liposome extruder to finally obtain a blank liposome with a particle size of 100 nm and uniform particle size distribution.

Step (5): the liposome prepared in Step (4) was charged into a dialysis bag with a molecular cutoff of 10000 for dialysis with a 10% aqueous sucrose solution as the dialysis medium at 4° C. overnight. The volume ratio of sample to dialysis medium was 1:1000. The dialysate was changed three times during dialysis, to completely remove the ammonium methanesulfonate in the external aqueous phase of liposome, and give a blank liposome composed of an external aqueous phase consisting of 10% sucrose, an internal aqueous phase of ammonium methanesulfonate solution, and a phospholipid bilayer. The internal and the external aqueous phases of the liposome had a certain pH gradient and ammonium methanesulfonate concentration gradient. In particular, the internal aqueous phase of the blank liposome was 650 mM aqueous ammonium methanesulfonate solution (pH4.0-6.0), and the external aqueous phase of the blank liposome was an aqueous sucrose solution with a mass fraction of 10%.

Step (6): the blank liposome suspension obtained in Step (5) of which the internal aqueous phase was an ammonium methanesulfonate solution was mixed with an aqueous solution of irinotecan hydrochloride with a concentration of 10 mg/ml at a volume ratio of 1:1 and incubated at 50-60° C. for 10-30 minutes, to give a liposome of which the internal aqueous phase contains irinotecan.

2.2. Characterization of Irinotecan Liposome 2.2.1. Determination of Particle Size of Irinotecan Liposome The irinotecan liposome prepared in this Embodiment was 50× diluted with ddH₂O, and analyzed for particle size by Zetasizer ZS90 (Malvern Company, UK). The specific results are shown in Table 3. Table 3 shows that the drug-loaded liposome has a particle size of about 100 nm, and the particle size distribution (PDI) is less than 0.1. In addition, the drug-unloaded blank liposome also has a particle size of about 100 nm, and the particle size distribution (PDI) is less than 0.1.

2.2.2. Determination of Encapsulation Efficiency of Irinotecan Liposome

To the prepared irinotecan liposome was added an appropriate amount of Dowex resin (Sigma Aldrich Company), and the mixture was fully shaken to adsorb the unencapsulated irinotecan. After standing, 200 ul of supernatant was taken, and detected by UV detection analysis method (Embodiment 1) for the irinotecan contents in the liposome before and after the addition of resin.

The encapsulation efficiency (EE) of irinotecan liposome is calculated in accordance with the following equation:

$$EE\% = \frac{M\ inter}{M\ total} * 100\%$$

M$_{inter}$ is the content of irinotecan in the liposome preparation after the resin adsorbs free drug, that is, the amount of irinotecan encapsulated in the liposome; M$_{total}$ is the content of irinotecan in the liposome preparation before the resin adsorbs the drug, that is, the adding amount of irinotecan. The results are shown in Table 2. Table 2 shows that the irinotecan liposome prepared according to this method has good encapsulation efficiency, and can achieve the drug loading with a high drug-lipid ratio.

TABLE 2

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| | 0.86 | 0.1 | 100.06 | 0.046 | 95.28 |
| 8.91 | 2.58 | 0.3 | 100.08 | 0.035 | 88.91 |
| | 4.30 | 0.5 | 101.00 | 0.037 | 70.01 |

Particle size and encapsulation efficiency of irinotecan liposome including ammonium methanesulfonate solution as the internal aqueous phase Embodiment 3 Preparation and Characterization of Irinotecan Liposome Using Triethylamine Methanesulfonate Solution as the Internal Aqueous Phase The methanesulfonic acid used in this Embodiment was purchased from Sigma-Aldrich Company; and the triethylamine used was purchased from the Sinopharm Group.

2.131 ml of methanesulfonic acid solution was accurately taken, titrated with triethylamine to a pH of 4.0-6.0, and supplemented with ddH$_2$O to a volume of 50 ml to give a buffer of 650 mM of triethylamine methanesulfonate at a pH of 4.0-6.0;

an irinotecan liposome was prepared by the same method of Embodiment 2, except that in Step (3), the solution of lipids in ethanol obtained in Step (1) was added with 10 ml of 650 mM triethylamine methanesulfonate buffer with a pH of 4.0-6.0, instead of the ammonium methanesulfonate buffer.

The irinotecan liposome was characterized by the method of Embodiment 2. The results are shown in Table 3. Table 3 shows that the irinotecan liposome prepared in Embodiment 3 has an encapsulation efficiency of about 70%. Compared with the results of Embodiment 2, the liposome including triethylamine methanesulfonate as the internal aqueous phase of the liposome exhibits decreased encapsulation efficiency, indicating that the contribution of ammonium ion concentration gradient in active drug loading is better than that of triethylamine ion concentration gradient.

TABLE 3

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| | 0.86 | 0.1 | 102.10 | 0.031 | 82.41 |
| 8.91 | 2.58 | 0.3 | 102.40 | 0.043 | 76.92 |
| | 4.30 | 0.5 | 102.70 | 0.029 | 60.10 |

Particle size and encapsulation efficiency of irinotecan liposome including triethylamine methanesulfonate solution as the internal aqueous phase Embodiment 4 Preparation and Characterization of
Irinotecan Liposome Including Ammonium
4-Hydroxybenzenesulfonate Solution as the Internal
Aqueous Phase In this Embodiment, the 4-hydroxybenzenesulfonic acid used was purchased from Macklin Company; and the ammonium hydroxide used was purchased from Aladdin Company.

6.513 ml of 4-hydroxybenzenesulfonate solution was accurately taken, titrated with ammonium hydroxide to a pH of 4.0-6.0, supplemented with $ddH_2O$ to a volume of 50 ml to give a 650 mM ammonium 4-hydroxybenzenesulfonate buffer at a pH of 4.0-6.0.

An irinotecan liposome was prepared by the same method of Embodiment 2, except that in Step (3), the solution of lipids in ethanol obtained in Step (1) was added with 10 ml of 650 mM ammonium 4-hydroxybenzenesulfonate buffer (at a pH of 4.0-6.0), instead of ammonium methanesulfonate buffer.

The irinotecan liposome was characterized by the method of Embodiment 2. The results are shown in Table 4. Table 4 shows that the irinotecan liposome prepared in Embodiment 4 has good encapsulation efficiency.

TABLE 4

| Particle size and encapsulation efficiency of irinotecan liposome including ammonium 4-hydroxybenzenesulfonate solution as the internal aqueous phase | | | | | |
|---|---|---|---|---|---|
| Lipid concentration (mg/ml) | Drug concentration (mg/ml) | Drug-liposome ratio | Particle size after drug loading (nm) | PDI after drug loading | Encapsulation efficiency (%) |
| | 0.86 | 0.1 | 99.20 | 0.048 | 96.55 |
| 8.91 | 2.58 | 0.3 | 99.18 | 0.037 | 77.70 |
| | 4.30 | 0.5 | 98.65 | 0.045 | 60.19 |

Embodiment 5 Preparation and Characterization of
Irinotecan Liposome Including Triethylamine
4-Hydroxybenzenesulfonate Solution as the Internal
Aqueous Phase In this Embodiment, the triethylamine 4-hydroxybenzenesulfonate used was purchased from Macklin Company; and the triethylamine used was purchased from the Sinopharm Group.

6.513 ml of 4-hydroxybenzenesulfonate solution was accurately taken, titrated with triethylamine to a pH of 4.0-6.0, supplemented with $ddH_2O$ to a volume of 50 ml to give a 650 mM triethylamine 4-hydroxybenzenesulfonate buffer at a pH of 4.0-6.0.

An irinotecan liposome was prepared by the same method of Embodiment 2, except that in Step (3), the solution of lipids in ethanol obtained in Step (1) was added with 10 ml of 650 mM triethylamine 4-methanesulfonate buffer at a pH of 4.0-6.0, instead of the ammonium methanesulfonate buffer.

The irinotecan liposome was characterized by the method of Embodiment 2. The results are shown in Table 5. Table 5 shows that the irinotecan liposome prepared in Embodiment 5 has good encapsulation efficiency.

TABLE 5

| Particle size and encapsulation efficiency of irinotecan liposome including triethylamine 4-hydroxybenzenesulfonate solution as the internal aqueous phase | | | | | |
|---|---|---|---|---|---|
| Lipid concentration (mg/ml) | Drug concentration (mg/ml) | Drug-liposome ratio | Particle size after drug loading (nm) | PDI after drug loading | Encapsulation efficiency (%) |
| | 0.86 | 0.1 | 102.15 | 0.033 | 97.80 |
| 8.91 | 2.58 | 0.3 | 102.80 | 0.058 | 89.69 |
| | 4.30 | 0.5 | 102.55 | 0.065 | 62.93 |

Figure 3:
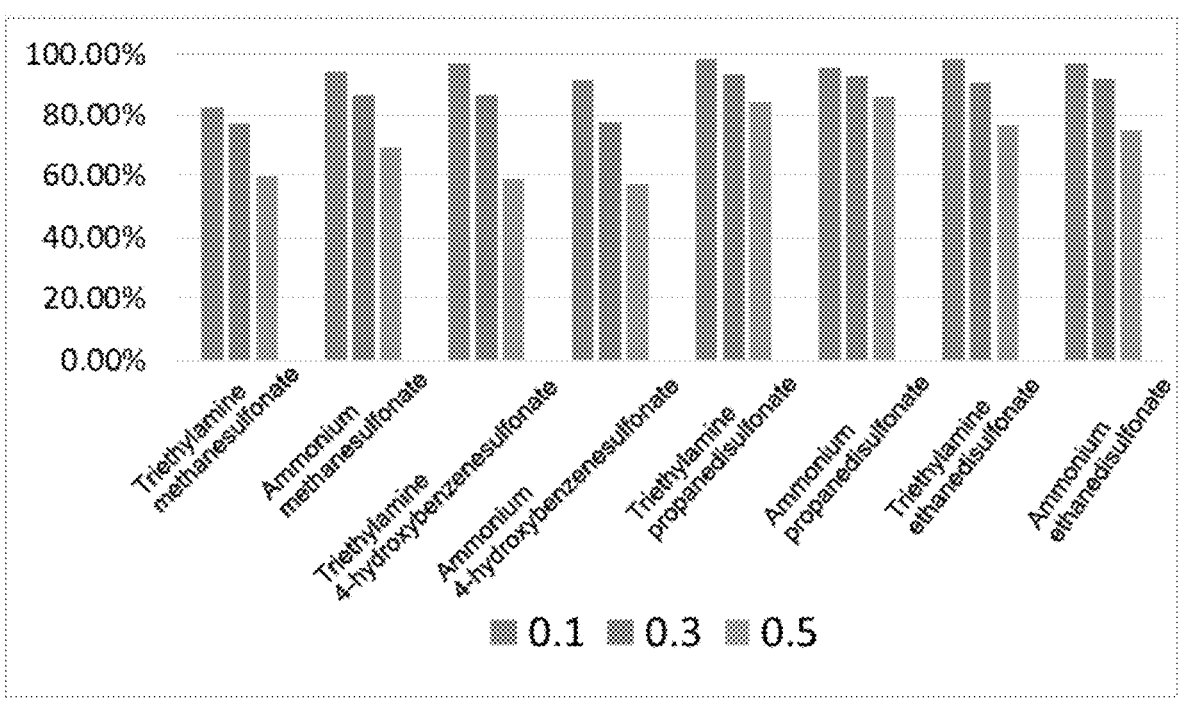
FIG. 3: encapsulation efficiency of irinotecan liposomes prepared at different gradients at three sets of different drug-liposome ratios (0.1, 0.3 and 0.5, respectively)

The effects of the four types of internal aqueous phases in Embodiments 2, 3, 4 and 5 on the drug loading capacity of irinotecan liposome are shown in FIG. 3.

Embodiment 6 Preparation and Characterization of Irinotecan Liposome Including Ammonium Ethanedisulfonate Solution as the Internal Aqueous Phase In this Embodiment, the ethanedisulfonic acid used was purchased from Alfa Aesar Company; and the ammonium hydroxide used was purchased from Aladdin Company.

3.1538 mg of ethanedisulfonic acid hydrate was accurately taken, titrated with ammonium hydroxide to a pH of 4.0-6.0, and supplemented with $ddH_2O$ to a volume of 50 ml to give a 325 mM ammonium ethanedisulfonate buffer at a pH of 4.0-6.0;

an irinotecan liposome was prepared by the same method of Embodiment 2, except that in Step (3), the solution of lipids in ethanol obtained in Step (1) was added with 10 ml of 325 mM ammonium ethanedisulfonate buffer at a pH of 4.0-6.0, instead of the ammonium methanesulfonate buffer.

The irinotecan liposome was characterized by the method of Embodiment 2. The results are shown in Table 6. Table 6 shows that the irinotecan liposome prepared in Embodiment 6 has good encapsulation efficiency.

TABLE 6

| Particle size and encapsulation efficiency of irinotecan liposome including ammonium ethanedisulfonate solution as the internal aqueous phase | | | | | |
|---|---|---|---|---|---|
| Lipid concentration (mg/ml) | Drug concentration (mg/ml) | Drug-liposome ratio | Particle size after drug loading (nm) | PDI after drug loading | Encapsulation efficiency (%) |
| 8.91 | 0.86 | 0.1 | 101.55 | 0.035 | 96.92 |
| | 2.58 | 0.3 | 101.90 | 0.048 | 92.17 |
| | 4.30 | 0.5 | 101.85 | 0.059 | 74.90 |

Embodiment 7 Preparation and Characterization of Irinotecan Liposome Including Triethylamine Ethanedisulfonate Solution as the Internal Aqueous Phase In this Embodiment, the ethionic acid used was purchased from Alfa Aesar Company; and the triethylamine used was purchased from the Sinopharm Group.

3.1535 mg of ethanedisulfonic acid hydrate was accurately taken, dissolved in $ddH_2O$, titrated with triethylamine to a pH of 4.0-6.0, and supplemented with $ddH_2O$ to a volume of 50 ml to give a 325 mM triethylamine ethanedisulfonate buffer at a pH of 4.0-6.0;

An irinotecan liposome was prepared by the same method of Embodiment 2, except that in Step (3), the solution of lipids in ethanol obtained in Step (1) was added with 10 ml of 325 mM triethylamine ethanedisulfonate buffer at a pH of 4.0-6.0, instead of the ammonium methanesulfonate buffer.

The irinotecan liposome was characterized by the method of Embodiment 2. The results are shown in Table 7. Table 7 shows that the irinotecan liposome prepared in Embodiment 7 has good encapsulation efficiency.

TABLE 7

| Particle size and encapsulation efficiency of irinotecan liposome including triethylamine ethanedisulfonate solution as the internal aqueous phase | | | | | |
|---|---|---|---|---|---|
| Lipid concentration (mg/ml) | Drug concentration (mg/ml) | Drug-liposome ratio | Particle size after drug loading (nm) | PDI after drug loading | Encapsulation efficiency (%) |
| 8.91 | 0.86 | 0.1 | 102.45 | 0.043 | 98.25 |
| | 2.58 | 0.3 | 101.98 | 0.060 | 90.43 |
| | 4.30 | 0.5 | 102.36 | 0.051 | 76.06 |

Embodiment 8 Preparation and Characterization of Irinotecan Liposome Including Ammonium Propanedisulfonate Solution as the Internal Aqueous Phase In this Embodiment, the propanedisulfonic acid used was purchased from Alfa Aesar Company; and the ammonium hydroxide used was purchased from Aladdin Company.

4.741 ml of propanedisulfonic acid solution was accurately taken, titrated with ammonium hydroxide to a pH of 4.0-6.0, and supplemented with ddH$_2$O to a volume of 50 ml to give a 325 mM ammonium propanedisulfonate buffer at a pH of 4.0-6.0;

an irinotecan liposome was prepared by the same method of Embodiment 2, except that in Step (3), the solution of lipids in ethanol obtained in Step (1) was added with 10 ml of 325 mM ammonium propanedisulfonate buffer at a pH of 4.0-6.0, instead of ammonium methanesulfonate buffer.

The irinotecan liposome was characterized by the method of Embodiment 2. The results are shown in Table 8. Table 8 shows that the irinotecan liposome prepared in Embodiment 8 has good encapsulation efficiency.

TABLE 8

Particle size and encapsulation efficiency of irinotecan liposome including ammonium propanedisulfonate solution as the internal aqueous phase

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| | 0.86 | 0.1 | 102.75 | 0.039 | 95.65 |
| 8.91 | 2.58 | 0.3 | 101.80 | 0.054 | 92.89 |
| | 4.30 | 0.5 | 102.34 | 0.062 | 85.91 |

Embodiment 9 Preparation and Characterization of Irinotecan Liposome Including Triethylamine Propanedisulfonate Solution as the Internal Aqueous Phase In this Embodiment, the propanedisulfonic acid used was purchased from Alfa Aesar Company; and the triethylamine used was purchased from the Sinopharm Group.

4.735 ml of 4-hydroxybenzenesulfonic acid solution was accurately taken, titrated with triethylamine to a pH of 4.0-6.0, and supplemented with ddH$_2$O to a volume of 50 ml to give a 325 mM triethylamine propanedisulfonate buffer at a pH of 4.0-6.0;

An irinotecan liposome was prepared by the same method of Example 2, except that in Step (2), to the solution of lipid in ethanol obtained in Step (1) was added 10 ml of 325 mM triethylamine propanedisulfonate buffer at a pH of 4.0-6.0, instead of the ammonium methanesulfonate buffer.

The irinotecan liposome was characterized by the method of Embodiment 2. The results are shown in Table 9. Table 9 shows that the irinotecan liposome prepared in Embodiment 9 has good encapsulation efficiency.

TABLE 9

Particle size and encapsulation efficiency of irinotecan liposome including triethylamine propanedisulfonate solution as the internal aqueous phase

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| | 0.86 | 0.1 | 101.87 | 0.047 | 98.39 |
| 8.91 | 2.58 | 0.3 | 102.16 | 0.054 | 93.25 |
| | 4.30 | 0.5 | 102.41 | 0.056 | 84.47 |

The effects of the eight types of internal aqueous phases in Embodiments 2-9 on the drug loading capacity of irinotecan liposome are shown in FIG. 3.

Embodiment 10 Study of In Vitro Release of Irinotecan Liposomes Including Different Sulfonates as the Internal Aqueous Phase At different drug-liposome ratios, the internal aqueous phases of the liposomes have different drug concentrations, so that the insoluble salts formed from the drug and the sulfonate ions are likely to have different structures, and thus may have different drug release rates. For comparing the in vitro release rates of irinotecan liposomes prepared by using different sulfonates (including ammonium and triethylamine salts) as the internal aqueous phase, in this Embodiment, the irinotecan liposomes used for in vitro release study all have the same drug-liposome ratio (0.3), same drug-loading concentration of 2.58 mg/ml, and same lipid concentration of 8.91 mg/ml.

Bovine serum albumin (BSA) for in vitro release study was purchased from Sangon Biotech (Shanghai) Co., Ltd.; and Dowex resin was purchased from Sigma-Aldrich Company.

The specific procedures of the in vitro release experiment of irinotecan liposome are as follows:

Step (1): 4.0152 g bovine serum albumin (BSA) powder was accurately taken and dissolved in 100 ml normal saline to form a 40 mg/ml albumin in normal saline solution (the protein concentration is comparable with the protein concentration of 50% plasma);

Step (2): the irinotecan liposomes including different monovalent sulfonate or disulfonate solutions (at a pH of 4.0-6.0) as the internal aqueous solution prepared in Embodiments 2-9 were used; the lipid concentration was 8.91 mg/ml, and the drug-liposome ratio (the molar ratio of drugs to liposomes) was 0.3.

Step (3): the liposome was 80× diluted with 40 mg/ml albumin in normal saline, a sufficient amount of Dowex resin was added to adsorb free drug to form a sink condition. The mixture was shaken at 37° C. at 100 rpm in a shaker (THZ-C constant temperature oscillator, China). The samples were collected at different time points (0 hr, 1 hr, 3 hrs, 6 hrs, 9 hrs and 24 hrs), and the supernatant was taken after standing. The content of irinotecan encapsulated in liposome was determined by the UV method, and the cumulative release rate of irinotecan at different time points was calculated.

For comparison, the present disclosure also prepares an irinotecan liposome including triethylamine sucrose octasulfate as the internal aqueous phase according to the specification of commercially available Onivyde, the lipid concentration is 8.91 mg/ml and the drug-liposome ratio is 0.3; and an irinotecan liposome includes 325 mM ammonium sulfate at a pH of 4.0-6.0 as the internal aqueous phase, the lipid concentration is 8.91 mg/ml and the drug-liposome ratio is 0.3. According to the above method, the in vitro release rates of irinotecan liposomes including triethylamine sucrose octasulfate and ammonium sulfate as the internal aqueous phase in albumin-normal saline were measured in parallel, and compared with the release rate of irinotecan liposome preparation provided by the present disclosure.

Figure 4:
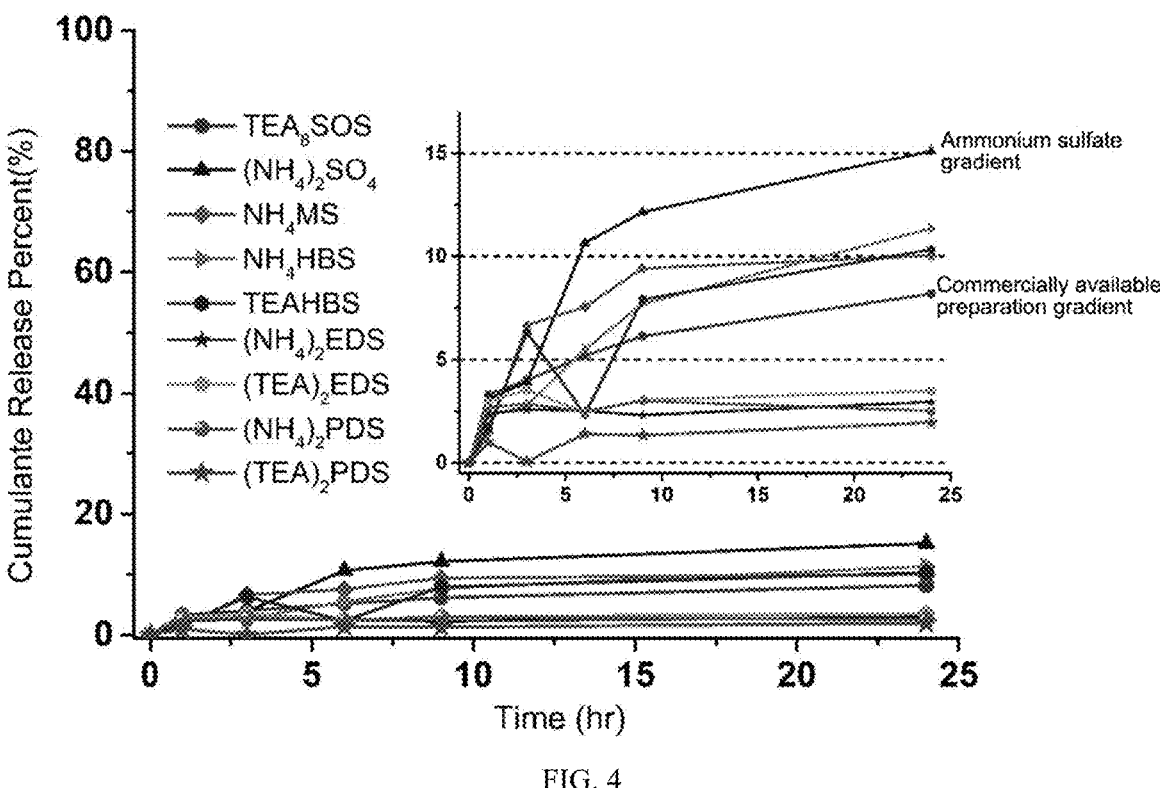
FIG. 4: a graph of cumulative release rate of irinotecan liposomes having different sulfonate solutions as internal aqueous phase in simulated plasma (TEA: triethylamine; MS: methanesulfonic acid; HBS: 4-hydroxybenzenesulfonic acid; EDS: ethionic acid; PDS: propanedisulfonic acid)

The in vitro cumulative release curves of individual groups of irinotecan liposomes are shown in FIG. 4. FIG. 4 shows that in the albumin saline solution, the irinotecan liposomes including ammonium methanesulfonate, ammonium 4-hydroxybenzenesulfonate, triethylamine 4-hydroxybenzenesulfonate, ammonium ethanedisulfonate, triethylamine ethanedisulfonate, ammonium propanedisulfonate and triethylamine propanedisulfonate solutions as the internal aqueous phases all have good sustained-release effect in vitro. Among them, the cumulative release percentage in 24 hours was 10.03% in the ammonium methanesulfonate group, 11.35% in the ammonium 4-hydroxybenzenesulfonate group, 10.32% in the triethylamine 4-hydroxybenzenesulfonate group, 1.03% in the ammonium ethanedisulfonate group, 3.49% in the triethylamine ethanedisulfonate group, 2.31% in the ammonium propanedisulfonate group and 1.96% in the triethylamine propanedisulfonate group. At the same time, in parallel detection, the cumulative release rate of triethylamine sucrose octasulfate group within 24 hours was 8.91%, and that of ammonium sulfate group was 15.34%. The results of in vitro release study show that the release rate of irinotecan liposome including monovalent sulfonate and disulfonate as the internal aqueous phase was significantly slower than that of irinotecan liposome including ammonium sulfate as the internal water phase.

Embodiment 11 Determination of Melting Point of Irinotecan Sulfonate

The methanesulfonic acid and hydroxybenzenesulfonic acid used in this Embodiment were purchased from Sigma-Aldrich Company.

Melting points can reflect the regularity of the internal structure of a compound. The higher the melting point of a salt is, the more regular its molecular arrangement is likely to be. For example, the melting point of a crystal is often higher than that of the amorphous. In order to investigate the potential structure of the salt formed by different sulfonates and irinotecan in the internal aqueous phase of liposome, this Embodiment prepared irinotecan sulfonate by directly mixing irinotecan hydrochloride with sulfonate solution, and determined the melting points of each salt.

The specific procedures are as follows:

(1) 2.131 ml of methanesulfonic acid solution was accurately taken, and 2.431 ml ammonium hydroxide was added. The mixture was supplemented with ddH2O to a volume of 50 ml to give a 650 mM aqueous ammonium methanesulfonate solution. 50.6 mg irinotecan hydrochloride was accurately taken and added into 1 ml of 650 mM aqueous ammonium methanesulfonate solution, shaking well.

(2) 2.131 ml of methanesulfonic acid solution was accurately taken, and 4.572 ml of triethylamine was added. The mixture was supplemented with ddH2O to a volume of 50 ml to give a 650 mM aqueous triethylamine methanesulfonate solution. 50.6 mg irinotecan hydrochloride was accurately taken and added into 1 ml of 650 mM aqueous triethylamine methanesulfonate solution, shaking well.

(3) 6.513 ml of 4-hydroxybenzenesulfonic acid solution was accurately taken, and 2.432 ml of ammonium hydroxide was added. The mixture was supplemented with ddH2O to a volume of 50 ml to give a 650 mM aqueous ammonium hydroxybenzenesulfonate solution. 50.6 mg irinotecan hydrochloride was accurately taken and added into 1 ml 650 mM aqueous ammonium hydroxybenzenesulfonate solution, shaking well.

(4) 6.513 ml of 4-hydroxybenzenesulfonic acid solution was accurately taken, and 5.866 ml of triethylamine was added. The mixture was supplemented with ddH2O to a volume of 50 ml to give a 650 mM aqueous triethylamine hydroxybenzenesulfonate solution. 50.6 mg irinotecan hydrochloride was accurately taken and added into 1 ml 650 mM aqueous triethylamine hydroxybenzenesulfonate solution, shaking well.

The above suspension of the irinotecan hydrochloride and sulfonate solution was heated in an oil bath for melting point determination. The results are shown in Table 10.

TABLE 10

| | Results of determining the melting points of different irinotecan sulfonates | | | |
|---|---|---|---|---|
| | Salt solution | | | |
| Temperature (° C.) | Ammonium methanesulfonate | Triethylamine methanesulfonate | Ammonium 4-hydroxybenzenesulfonate | Triethylamine 4-hydroxybenzenesulfonate |
| Initial Melting Point | 88 | 86 | 91 | 92 |
| Complete Melting Point | 94 | 93 | 97 | 99 |
| Melting Range | 6 | 7 | 6 | 7 |

Table 10 shows that the melting temperature of individual irinotecan sulfonates ranges from 86° C. to 99° C. By analysis of the results of melting experiments in combination with the results of DSC experiment, it can be concluded that when these sulfonate solutions are used as the internal aqueous phases of liposomes, they would form crystalline or amorphous insoluble salts with irinotecan ions in the internal aqueous phases of liposomes, so as to achieve the stable encapsulation of irinotecan and increase the storage stability of irinotecan liposomes.

Embodiment 12 High Resolution DSC Characterization of Irinotecan Liposome

Studies have shown that the formation of nanocrystals in the internal aqueous phase of liposome is conducive to improving the storage stability of liposome preparation and slowing down the drug release rate (Wei, X. et al., Cardinal role of Intralipid doxorubicin sulfate nanorod crystal in Doxil properties and performance [J]. ACso Mega 2018, 3 (3), 2508-2517).

In order to investigate the microstructure of the salts formed by monovalent sulfonate and disulfonates and irinotecan in the internal aqueous phases of liposomes, on the basis of the melting point determination in Embodiment 11, the thermodynamic behavior of irinotecan liposome prepared in Embodiments 2-9 was studied by high-resolution DSC, and compared with the self-made irinotecan liposome including triethylamine sucrose octasulfate and ammonium sulfate as the internal aqueous phases. All the irinotecan liposome samples which underwent DSC characterization had a drug-liposome ratio of 0.3, a lipid concentration of 8.9 mg/ml, an average particle size of 100 nm, and a PDI of less than 0.1.

The differential scanning calorimeter (DSC) used in this Embodiment is capillary DSC of GE Company (US). The scanning temperature is 10-120° C., and the scanning speed is 1° C./min.

Figure 5:
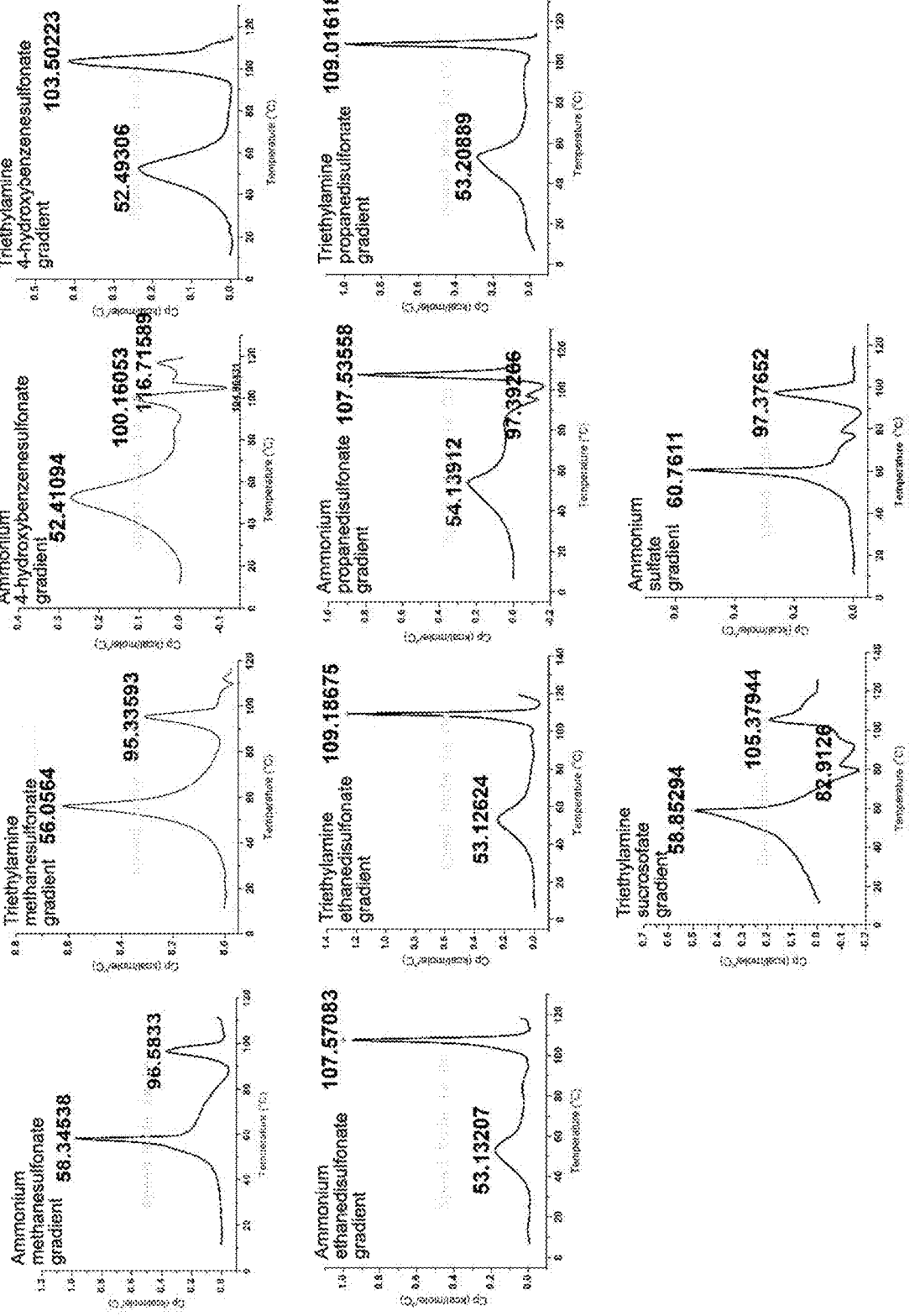
FIG. 5: differential thermal scanning diagrams of irinotecan liposomes prepared with different sulfonate gradients, triethylamine sucrosofate gradients and ammonium sulfate gradients.

The specific procedures are as follows:

Irinotecan liposomes including different sulfonate solutions as the internal aqueous phases prepared in Embodiments 2-9 were filtered by 0.22 um filter membrane, and then manually added into the capillary DSC sample pool (about 200 ul), with 10% sucrose solution as the control, heated and scanned, and the thermodynamic diagram was recorded. According to the method described in literatures (Wei, X. et al., Insights into composition/structure/function relationships of Doxil® gained from "high-sensitivity" differential scanning calorimetry [J]. Eur J Pharm Biopharm 2016, 104, 260-270), the obtained thermodynamic diagram was treated, and the thermodynamic parameters were calculated according to the molar concentration of irinotecan encapsulated in each liposome. The results are shown in FIG. 5. The main thermodynamic parameters of irinotecan hydrochloride liposome in each group are shown in Table 11.

TABLE 11

| | Study of main pharmacokinetic parameters of irinotecan liposomes including different sulfonates as the internal aqueous phase | |
|---|---|---|
| Sulfonates | Phase transition temperature of lipid bilayers (° C.) | Melting temperature of irinotecan sulfonate in internal aqueous phase (° C.) |
| Triethylamine sucrosofate | 58.85 | 105.38 |
| Ammonium sulfate | 60.76 | 97.38 |
| Ammonium methanesulfonate | 58.35 | 96.58 |
| Triethylamine methanesulfonate | 56.05 | 95.53 |
| Ammonium 4-hydroxybenzenesulfonate | 52.41 | 100.16, 116.71 (Melting temperature after recrystallization) |
| Triethylamine 4-hydroxybenzenesulfonate | 52.49 | 103.50 |
| Ammonium ethanedisulfonate | 53.13 | 107.57 |
| Triethylamine ethanedisulfonate | 53.13 | 109.18 |
| Ammonium propanedisulfonate | 54.14 | 107.53 |
| Triethylamine propanedisulfonate | 53.20 | 109.16 |

DSC results showed that the sulfonate in the internal aqueous phase of irinotecan liposome formed a regular structure with a high melting point. This form is conducive to stable drug loading and sustained release of the preparation. Combined with the in vitro release results of Embodiment 10, the irinotecan liposome including ammonium methanesulfonate, ammonium 4-hydroxybenzenesulfonate, triethylamine 4-hydroxybenzenesulfonate solution and four groups of disulfonate solutions as internal aqueous phases have good in vitro release effect.

Embodiment 12

In the present disclosure, other kinds of irinotecan liposomes were prepared and characterized by reference to Embodiment 2 and Embodiment 6.

Type 1: it differs from the method for preparing the irinotecan liposome in Embodiment 2 in that in Step (2), an ammonium methanesulfonate solution was used to adjust pH to prepare an 800 mM ammonium methanesulfonate buffer at a pH of 9.0; in Step (4), a blank liposome having a particle size of 200 nm was obtained; and in Step (6), the mixing was performed with an aqueous solution of irinotecan hydrochloride with a concentration of 15 mg/ml; and the remainder is the same.

Type 2: it differs from the method of preparing the irinotecan liposome in Embodiment 2 in that in Step (2), an ammonium methanesulfonate solution was used to adjust pH to prepare a 100 mM ammonium methanesulfonate buffer at a pH of 4.5; in Step (4), a blank liposome having a particle size of 30 nm was obtained; and in Step (6), the mixing was performed with an aqueous solution of irinotecan hydrochloride with a concentration of 10 mg/ml; and the remainder is the same.

Type 3: it differs from the method of preparing the irinotecan liposome in Embodiment 2 in that in Step (2), an ammonium methanesulfonate solution was used to adjust pH to prepare a 200 mM ammonium methanesulfonate buffer at a pH of 5.0; in Step (4), a blank liposome having a particle size of 50 nm was obtained; and in Step (6), the mixing was performed with an aqueous solution of irinotecan hydrochloride with a concentration of 13 mg/ml; and the remainder is the same.

Type 4: it differs from the method of preparing the irinotecan liposome in Embodiment 2 in that in Step (2), an ammonium methanesulfonate solution was used to adjust pH to prepare a 700 mM ammonium methanesulfonate buffer at a pH of 8.0; in Step (4), a blank liposome having a particle size of 120 nm was obtained; and in Step (6), the mixing was performed with an aqueous solution of irinotecan hydrochloride with a concentration of 14 mg/ml; and the remainder is the same.

Type 5: it differs from the method of preparing the irinotecan liposome in Embodiment 6 in that in Step (2), a solution of ethionic acid hydrate was used to adjust pH to prepare a 500 mM ammonium ethanedisulfonate buffer at a pH of 6.0; in Step (4), a blank liposome having a particle size of 90 nm was obtained; and in Step (6), the mixing was performed with an aqueous solution of irinotecan hydrochloride with a concentration of 14 mg/ml; and the remainder is the same.

Type 6: it differs from the method of preparing the irinotecan liposome in Embodiment 6 in that in Step (2), a solution of ethionic acid hydrate was used to adjust pH to prepare a 50 mM ammonium ethanedisulfonate buffer at a pH of 4.0; in Step (4), a blank liposome having a particle size of 110 nm was obtained; and in Step (6), the mixing was performed with an aqueous solution of irinotecan hydrochloride with a concentration of 12 mg/ml; and the remainder is the same.

Type 7: it differs from the method of preparing the irinotecan liposome in Embodiment 6 in that in Step (2), a solution of ethionic acid hydrate was used to adjust pH to prepare a 100 mM ammonium ethanedisulfonate buffer at a pH of 4.5; in Step (4), a blank liposome having a particle size of 80 nm was obtained; and in Step (6), the mixing was performed with an aqueous solution of irinotecan hydrochloride with a concentration of 13 mg/ml; and the remainder is the same.

Type 8: it differs from the method of preparing the irinotecan liposome in Embodiment 6 in that in Step (2), a solution of ethionic acid hydrate was used to adjust pH to prepare a 400 mM ammonium ethanedisulfonate buffer at a pH of 7.5; in Step (4), a blank liposome having a particle size of 150 nm was obtained; and in Step (6), the mixing was performed with an aqueous solution of irinotecan hydrochloride with a concentration of 13 mg/ml; and the remainder is the same.

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| Type 1 Particle size and encapsulation efficiency of irinotecan liposome including ammonium methanesulfonate solution as the internal aqueous phase | | | | | |
| | 0.86 | 0.1 | 200.10 | 0.041 | 95.28 |
| 8.91 | 2.58 | 0.3 | 201.20 | 0.053 | 88.91 |
| | 4.30 | 0.5 | 199.70 | 0.025 | 70.01 |
| Type 2 Particle size and encapsulation efficiency of irinotecan liposome including ammonium methanesulfonate solution as the internal aqueous phase | | | | | |
| | 0.86 | 0.1 | 30.57 | 0.065 | 94.35 |
| 8.91 | 2.58 | 0.3 | 29.85 | 0.058 | 87.94 |
| | 4.30 | 0.5 | 30.22 | 0.061 | 71.14 |
| Type 3 Particle size and encapsulation efficiency of irinotecan liposome including ammonium methanesulfonate solution as the internal aqueous phase | | | | | |
| | 0.86 | 0.1 | 50.16 | 0.046 | 94.76 |
| 8.91 | 2.58 | 0.3 | 50.40 | 0.052 | 89.22 |
| | 4.30 | 0.5 | 49.60 | 0.038 | 70.52 |

-continued

| Lipid concentration (mg/ml) | Drug concentration (mg/ml) | Drug-liposome ratio | Particle size after drug loading (nm) | PDI after drug loading | Encapsulation efficiency (%) |
|---|---|---|---|---|---|
| Type 4 Particle size and encapsulation efficiency of irinotecan liposome including ammonium methanesulfonate solution as the internal aqueous phase | | | | | |
| | 0.86 | 0.1 | 121.10 | 0.051 | 95.86 |
| 8.91 | 2.58 | 0.3 | 120.46 | 0.054 | 87.21 |
| | 4.30 | 0.5 | 119.78 | 0.042 | 69.51 |
| Type 5 Particle size and encapsulation efficiency of irinotecan liposome including ammonium ethanedisulfonate solution as the internal aqueous phase | | | | | |
| | 0.86 | 0.1 | 90.15 | 0.041 | 85.21 |
| 8.91 | 2.58 | 0.3 | 91.46 | 0.049 | 77.62 |
| | 4.30 | 0.5 | 89.74 | 0.034 | 58.19 |
| Type 6 Particle size and encapsulation efficiency of irinotecan liposome including ammonium ethanedisulfonate solution as the internal aqueous phase | | | | | |
| | 0.86 | 0.1 | 110.10 | 0.065 | 82.31 |
| 8.91 | 2.58 | 0.3 | 111.20 | 0.058 | 73.98 |
| | 4.30 | 0.5 | 109.65 | 0.061 | 58.95 |
| Type 7 Particle size and encapsulation efficiency of irinotecan liposome including ammonium ethanedisulfonate solution as the internal aqueous phase | | | | | |
| | 0.86 | 0.1 | 80.10 | 0.046 | 80.25 |
| 8.91 | 2.58 | 0.3 | 81.45 | 0.052 | 74.72 |
| | 4.30 | 0.5 | 80.35 | 0.038 | 61.18 |
| Type 8 Particle size and encapsulation efficiency of irinotecan liposome including ammonium ethanedisulfonate solution as the internal aqueous phase | | | | | |
| | 0.86 | 0.1 | 150.10 | 0.051 | 83.21 |
| 8.91 | 2.58 | 0.3 | 151.46 | 0.054 | 72.62 |
| | 4.30 | 0.5 | 148.98 | 0.042 | 60.96 |

The above examples only illustrate the principle and efficacy of the present disclosure, and are not used to limit the present disclosure. Any skilled man can modify or change the aforesaid examples without departing from the spirit and scope of the present disclosure. Therefore, all equivalent modifications or changes made by persons skilled in the art without departing from the spirit and technical idea disclosed by the present disclosure shall still be encompassed by the appending claims of the present disclosure.

The invention claimed is:

1. An irinotecan liposome preparation, comprising an irinotecan liposome and an external aqueous phase located outside a liposome membrane, wherein the irinotecan liposome comprises: irinotecan, a liposome, and an internal aqueous phase located inside a liposome membrane, the irinotecan being encapsulated in the internal aqueous phase;

wherein the internal aqueous phase comprises an aqueous sulfonate solution; and the external aqueous phase is a physiological isotonic solution;

wherein the aqueous sulfonate solution comprises disulfonate;

wherein the disulfonate is selected from the group consisting of ammonium ethanedisulfonate, ammonium propanedisulfonate, triethylamine ethanedisulfonate, and triethylamine propanedisulfonate;

wherein a sulfonate gradient exists between the internal aqueous phases inside the liposome membrane and the external aqueous phase outside the liposome membrane.

2. The irinotecan liposome preparation according to claim 1, wherein an irinotecan cation and a sulfonate anion in the internal aqueous phase form an insoluble salt.

3. The irinotecan liposome preparation according to claim 1, characterized by comprising one or more of the followings: a. the internal aqueous phase of the liposome has a pH value of 4.0-9.0; b. in the irinotecan liposome preparation, the irinotecan has a concentration of greater than or equal to 0.1 mg/ml; c. in the irinotecan liposome preparation, the irinotecan has an encapsulation efficiency of greater than or equal to 85%.

4. An irinotecan liposome preparation of claim 1 prepared by the following method;

(1) preparing a blank liposome, of which both an internal aqueous phase and an external aqueous phase comprise an aqueous sulfonate solution;

(2) preparing a blank liposome, of which the internal aqueous phase comprises an aqueous sulfonate solution and the external aqueous phase comprises a physiological isotonic solution, to form a sulfonate concentration gradient between the internal and the external aqueous phases of the blank liposome; and (3) mixing the blank liposome obtained in Step (2) with an aqueous solution of an irinotecan soluble salt, incubating the mixture, and removing the free soluble irinotecan salt to obtain the irinotecan liposome.

* * * * *